United States Patent
Chen et al.

(10) Patent No.: US 11,988,659 B2
(45) Date of Patent: May 21, 2024

(54) NANOPORE ARRAYS

(71) Applicant: Roche Sequencing Solutions, Inc., Pleasanton, CA (US)

(72) Inventors: Roger J. A. Chen, Saratoga, CA (US); David J. Fullagar, Los Gatos, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 918 days.

(21) Appl. No.: 16/948,372

(22) Filed: Sep. 15, 2020

(65) Prior Publication Data

US 2020/0408736 A1 Dec. 31, 2020

Related U.S. Application Data

(63) Continuation of application No. 15/983,426, filed on May 18, 2018, now Pat. No. 10,809,244, which is a continuation of application No. 15/462,483, filed on Mar. 17, 2017, now Pat. No. 10,012,637, which is a continuation of application No. 13/759,701, filed on Feb. 5, 2013, now Pat. No. 9,759,711.

(51) Int. Cl.
*G01N 33/487* (2006.01)
*G11C 7/00* (2006.01)
*G11C 16/34* (2006.01)

(52) U.S. Cl.
CPC ......... *G01N 33/48721* (2013.01); *G11C 7/00* (2013.01); *G11C 16/34* (2013.01)

(58) Field of Classification Search
CPC ..... G01N 33/48721; G11C 16/34; G11C 7/00
See application file for complete search history.

(56) References Cited

U.S. PATENT DOCUMENTS

| | | | |
|---|---|---|---|
| 6,493,776 B1 * | 12/2002 | Courtright | G06F 13/4217 710/110 |
| 2005/0090017 A1 * | 4/2005 | Morales | G01N 1/44 422/536 |
| 2011/0193570 A1 * | 8/2011 | Chen | G01N 33/48721 324/654 |

* cited by examiner

*Primary Examiner* — Jennifer Wecker
(74) *Attorney, Agent, or Firm* — Roche Sequencing Solutions, Inc.

(57) ABSTRACT

A method of analyzing molecules using a nanopore array including a plurality of cells included on a chip is disclosed. Nanopores are caused to be formed in at least a portion of the plurality of the cells. A first physical measurement of the nanopores is evaluated. It is determined whether to cause the molecules to interact with the nanopores. At least a portion of the nanopores is caused to interact with the molecules. A second physical measurement of the nanopores that indicates a property of the molecules is evaluated. It is determined whether to cause the nanopores to be reformed so that the cells may be reused to interact with additional molecules.

6 Claims, 7 Drawing Sheets

NANOPORE ARRAYS

CROSS REFERENCE TO OTHER APPLICATIONS

This application is a continuation of U.S. patent application Ser. No. 15/983,426, filed May 18, 2018, titled "NANOPORE ARRAYS", which is a continuation of U.S. patent application Ser. No. 15/462,483, entitled NANOPORE ARRAYS, filed Mar. 17, 2017, now U.S. Pat. No. 10,012,637, which is a continuation of U.S. patent application Ser. No. 13/759,701, now U.S. Pat. No. 9,759,711, entitled NANOPORE ARRAYS, filed Feb. 5, 2013, both of which are incorporated herein by reference for all purposes.

BACKGROUND OF THE INVENTION

Advances in micro-miniaturization within the semiconductor industry in recent years have enabled biotechnologists to begin packing their traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

DETAILED DESCRIPTION

Figure 1:
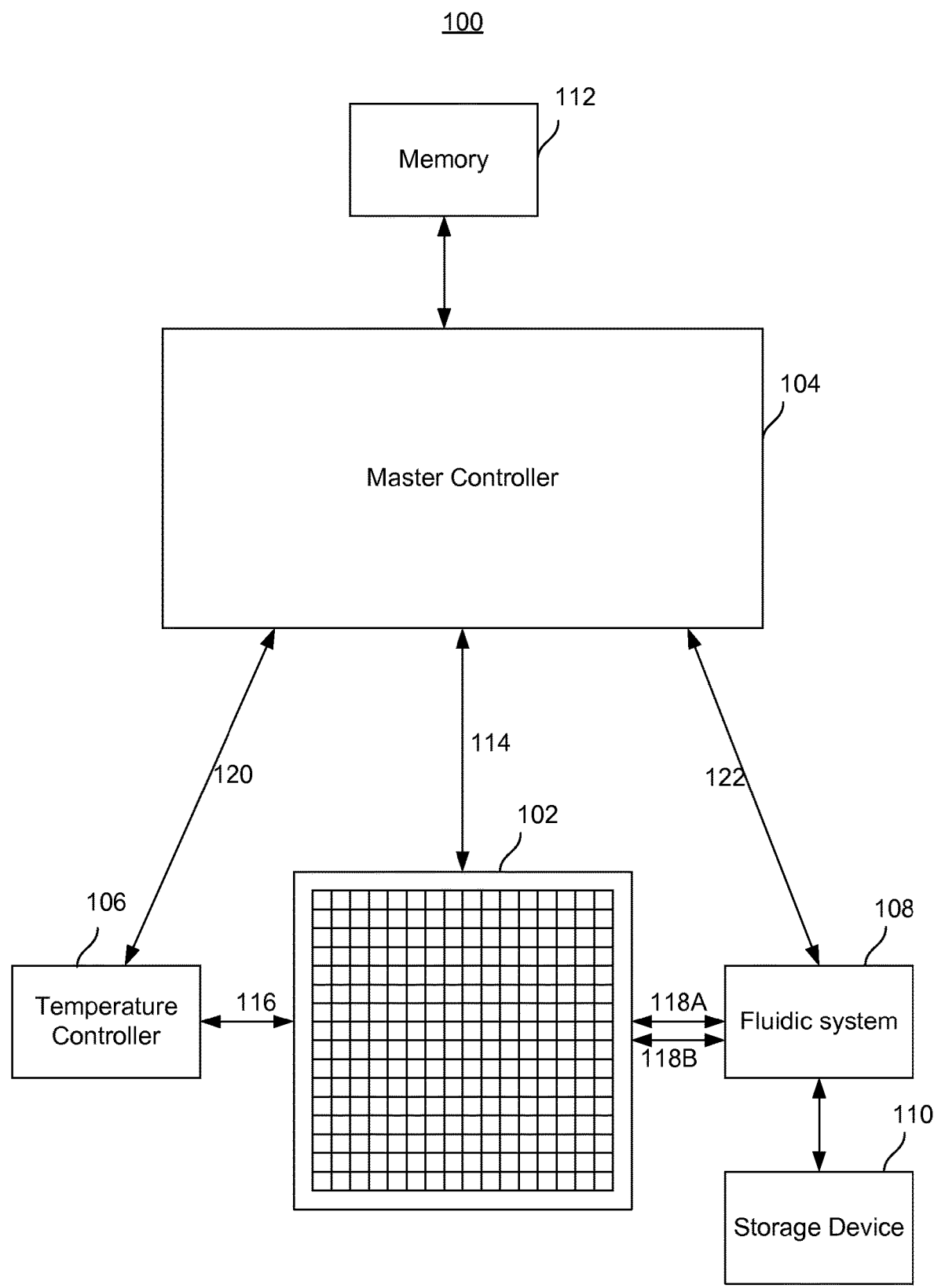
FIG. 1 is a block diagram illustrating an embodiment of a system 100 for analyzing molecules using nanopore devices.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

In various embodiments, the techniques described herein are implemented in a variety of systems or forms. In some embodiments, the techniques are implemented in hardware as an application-specific integrated circuit (ASIC) or a field-programmable gate array (FPGA). In some embodiments, a processor (e.g., an embedded one such as an ARM core) is used where the processor is provided or loaded with instructions to perform the techniques described herein. In some embodiments, the technique is implemented as a computer program product which is embodied in a computer readable storage medium and comprises computer instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Advances in micro-miniaturization within the semiconductor industry in recent years have enabled biotechnologists to begin packing their traditionally bulky sensing tools into smaller and smaller form factors, onto so-called biochips. These chips are essentially miniaturized laboratories that can perform hundreds or thousands of simultaneous biochemical reactions. Biochips enable researchers to quickly screen large numbers of biological analytes for a variety of purposes, from disease diagnosis to detection of bioterrorism agents.

Typically, a biochip includes a large array of cells. For example, a biochip for nucleotide sequencing may contain thousands or millions of single cells in an array. Each cell includes a molecular complex composed of monomers that make up an oligomeric nanopore. Each cell may further include a single strand of DNA, and anything bound to that single strand of DNA. The nanopore is a small hole in an electrically insulating membrane that can be used as a single-molecule detector. A nanopore may be formed using a biological material, such as α-hemolysin or MspA. A nanopore may be formed using a solid-state material, such as a semiconductor material. When a small voltage is applied across a molecular complex containing a nanopore, an ionic current through the molecular complex can be measured to provide information about the structure of a molecule transiting the molecular complex. In a single cell of the array, an electrical circuit may be used for controlling the electrical stimulus applied across a lipid bilayer which contains a nanopore, and for detecting and analyzing the electrical patterns, or signatures, of a molecule passing through the nanopore.

FIG. 1 is a block diagram illustrating an embodiment of a system 100 for analyzing molecules using nanopore devices. System 100 includes a nanopore array 102, a master controller 104, a temperature controller 106, a fluidic system 108, a storage device 110 for storing extracted results, and a memory 112. In some embodiments, some of the modules may be combined together as a single module, and some of the modules may be optional. In some embodiments, the cells of nanopore array 102 and the nanopore devices within the cells are individually controllable and individually addressable by other modules of system 100, including by master controller 104, temperature controller 106, and fluidic system 108. In some embodiments, performance data or other data corresponding to each of the cells may be sent from nanopore array 102 to other modules in system 100. Control, address, performance, or other data signals may be communicated between nanopore array 102 and other modules in system 100 via signal lines 114, 116, and 118A, respectively.

In some embodiments, the cells of nanopore array 102 and the nanopore devices within the cells are individually controllable and individually addressable by master controller 104. This allows master controller 104 to control each of the cells or each group of cells in nanopore array 102 such that the particular cell or particular group of cells performs different functions or transits through different states independently, without affecting the functioning or progress of other cells or other groups of cells in nanopore array 102. In one example, a mal-functioning cell in nanopore array 102 may be put in a state (e.g., disabled state) by master controller 104 such that the mal-functioning cell does not affect the functioning of other cells in nanopore array 102. For example, if a lipid bilayer fails to form in a particular cell, the cell may be disabled such that no electrical stimulus is applied to the cell; otherwise, the cell may draw a large current, which may affect the performance of other cells in nanopore array 102.

Figure 2:
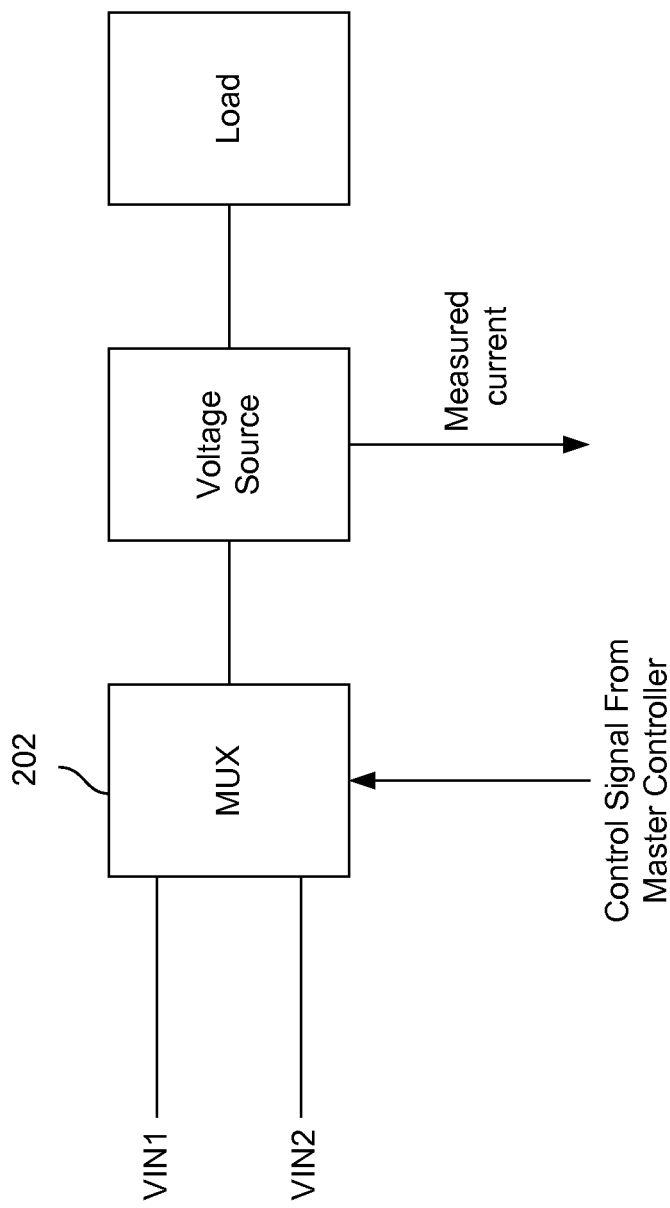
FIG. 2 is a block diagram illustrating an embodiment for applying a voltage stimulus to a cell in nanopore array 102.

In another example, master controller 104 may send control signals to nanopore array 102 such that different stimuli are applied to different cells or groups of cells. For example, a first stimulus (e.g., a voltage) is applied to a first group of cells and a second stimulus is applied to a second group of cells at time ti. The first stimulus may be a stimulus corresponding to a particular state of a cell, and the second stimulus may be a stimulus corresponding to a different state of a cell. The stimulus that is applied to the first group of cells may vary over time, as the first group of cells transits from one state to another. FIG. 2 is a block diagram illustrating an embodiment for applying a voltage stimulus to a cell in nanopore array 102. As shown in FIG. 2, control signals from master controller 104 may be used as input to a multiplexer 202 to select one of two voltages that can be applied to a cell in nanopore array 102.

In some embodiments, performance or other data corresponding to each of the cells may be received by master controller 104. By monitoring the performance or other data of the cells, master controller 104 may determine any state transitions of the cells. The state information of the cells may be stored in memory 112 by master controller 104. In addition, if the overall performance of nanopore array 102 falls below a certain threshold, master controller 104 may reset and re-initialize nanopore array 102 such that any processes running on nanopore array 102 may be terminated or restarted again. In some embodiments, nanopore array 102 may also be reused multiple times. For example, nanopore array 102 may be used for analyzing different types of samples during different runs. In another example, nanopore array 102 may be reused for analyzing a single type of samples over multiple runs. In some embodiments, nanopore array 102 may be reused after the contents in nanopore array 102 have been flushed out or rinsed out by master controller 104 and fluidic system 108.

In some embodiments, the cells of nanopore array 102 are individually controllable and individually addressable by temperature controller 106 via signal line 116. Temperature or other data corresponding to a cell may be received by temperature controller 106 via signal line 116. Depending on the state or condition of a particular cell or a group of cells, different temperature stimuli may be applied to the cell or group of cells by temperature controller 106. In some embodiments, temperature controller 106 receives state information of the cells via signal line 120 and applies the appropriate temperature stimuli to the cells in nanopore array 102 at least in part based on the state information. In some embodiments, temperature controller 106 receives control signal via signal line 120 from master controller 104, and then temperature controller 106 applies the appropriate temperature stimuli to the cells in nanopore array 102 based on the received control signal.

In some embodiments, the cells of nanopore array 102 are individually controllable and individually addressable by fluidic system 108. The control and address information is communicated between nanopore array 102 and fluidic system 108 via signal lines 118A. Different contents may be delivered in and out of the individual cells of nanopore array 102 via channels 118B. The contents may be any fluids or reagents that are used for the operations within the cells of nanopore array 102, including saline solution for rinsing, samples to be analyzed by nanopore array 102, lipid bilayer forming reagent, nanopore forming reagent, gas catalyst, and the like. The contents delivered out of nanopore array 102 may be any molecules that are extracted from the samples that have been analyzed by nanopore array 102, and the extracted molecules may be further delivered to a storage device 110 by fluidic system 108. The contents may be in any form, including liquid or gas. Depending on the state or condition of a particular cell or a group of cells, different fluids may be delivered to or from the cell or group of cells by fluidic system 108. In some embodiments, fluidic system 108 receives state information of the cells via signal line 122 and delivers the appropriate fluid to or from the cells in nanopore array 102 at least in part based on the state information. In some embodiments, fluidic system 108 receives control signal via signal line 122 from master controller 104, and then fluidic system 108 delivers the appropriate fluid to or from the cells in nanopore array 102 based on the received control signal. In some embodiments, nanopore array 102 may be reused after the contents in nanopore array 102 have been flushed out or rinsed out by master controller 104 and fluidic system 108.

Nanopore array 102 includes a large array of cells. Each cell includes a nanopore device for analyzing and characterizing molecules. Within a nanopore device, a lipid bilayer is formed, and a nanopore structure is then formed on the lipid bilayer. The nanopore structure has a nanopore that is large enough for enclosing at least a portion of a molecule that is being analyzed or passing at least a portion of the molecule between the two sides of the lipid bilayer. The nanopore device also includes a sample chamber for holding a solution of the analyzed molecules. The solution may be provided over the lipid bilayer for introducing the analyzed molecules for characterization. The nanopore device further includes means for providing electrical stimulus, sensing electrical characteristics, detecting and processing signal of the nanopore device.

Figure 3:
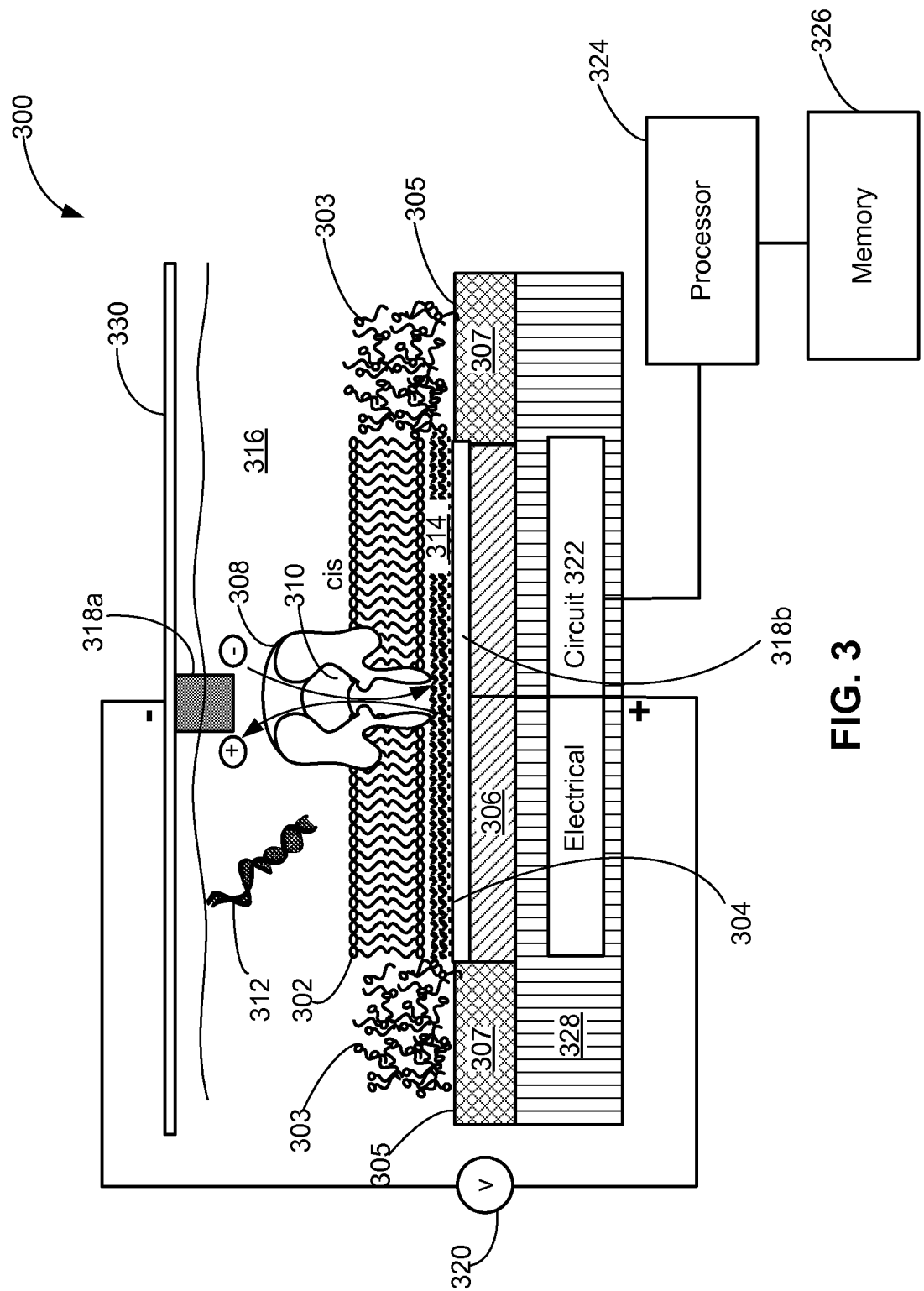
FIG. 3 is a diagram illustrating an embodiment of a nanopore device 300 within a cell of nanopore array 102.

FIG. 3 is a diagram illustrating an embodiment of a nanopore device 300 within a cell of nanopore array 102. Nanopore device 300 includes a lipid bilayer 302 formed on a lipid bilayer compatible surface 304 of a conductive solid substrate 306. Lipid bilayer compatible surface 304 may be isolated by lipid bilayer incompatible surfaces 305, and conductive solid substrate 306 may be electrically isolated by insulating materials 307. Lipid bilayer 302 may be surrounded by an amorphous lipid 303 formed on lipid bilayer incompatible surfaces 305.

In some embodiments, lipid bilayer 302 is embedded with a single nanopore structure 308 having a nanopore 310 large enough for passing at least a portion of a molecule 312 being characterized and/or small ions (e.g., $Na^+$, $K^+$, $Ca^{2+}$, $Cl^-$) between the two sides of lipid bilayer 302. A layer of water molecules 314 (also referred to as an aqueous film 314) may be adsorbed on lipid bilayer compatible surface 304 and sandwiched between lipid bilayer 302 and lipid bilayer compatible surface 304. Aqueous film 314 adsorbed on the hydrophilic lipid bilayer compatible surface 304 may promote the ordering of lipid molecules and facilitate the formation of lipid bilayer 302 on lipid bilayer compatible surface 304.

A sample chamber 316 may be provided over lipid bilayer 302 for introducing a sample for characterization. The sample may be a solution of molecule 312 that is being characterized. The solution may be an aqueous solution containing electrolytes and buffered to an optimum ion concentration and maintained at an optimum pH to keep nanopore 310 open. In some embodiments, sample chamber 316 receives the sample from fluidic system 108. The sample may also be flushed out of nanopore device 300 by fluidic system 108 after the characterization of the sample has been performed. Sample chamber 316 may also be rinsed with saline solution by fluidic system 108 such that nanopore device 300 may be reused again.

Nanopore device 300 includes a pair of electrodes 318 (including a negative node 318a and a positive node 318b) coupled to a variable voltage source 320 for providing electrical stimulus (e.g., voltage bias) across the lipid bilayer 302 and for sensing the electrical characteristics of the lipid bilayer 302 (e.g., resistance, capacitance, and ionic current flow). The surface of the negative positive electrode 318b is or forms a part of the lipid bilayer compatible surface 304. The conductive solid substrate 306 may be coupled to or forms a part of one of the electrodes 318. Nanopore device 300 may also include an electrical circuit 322 for controlling electrical stimulation and for processing the signal detected. In some embodiments, the variable voltage source 320 is included as a part of the electrical circuit 322. The electrical circuitry 322 may include amplifiers, integrators, noise filters, feedback control logic, and/or various other components. In some embodiments, the electrical circuitry 322 may be an integrated electrical circuitry integrated within a silicon substrate 328 and may be further coupled to a computer processor 324 coupled to a memory 326. For example, computer processor 324 may be a portion of master controller 104, and memory 326 may be memory 112 that is coupled to master controller 104. Master controller 104 may control the various components of nanopore device 300 via electrical circuit 322. Master controller 104 may also receive data collected by nanopore device 300 via electrical circuit 322.

The lipid bilayer compatible surface 304 can be formed from various materials that are suitable for ion transduction and gas formation to facilitate lipid bilayer formation. In some embodiments, conductive or semi-conductive hydrophilic materials as opposed to insulating hydrophilic materials are preferred because they may allow better detection of a change in the lipid bilayer electrical characteristics. Example materials include Ag—AgCl, Ag—Au alloy, Ag—Pt alloy, or doped silicon or other semiconductor materials.

The lipid bilayer incompatible surface 305 can be formed from various materials that are not suitable for lipid bilayer formation and they are typically hydrophobic. In some embodiments, a non-conductive hydrophobic material is preferred, since it electrically insulates the lipid bilayer regions in addition to separating the lipid bilayer regions from each other. Example lipid bilayer incompatible materials include silicon nitride (e.g., $Si_3N_4$) and Teflon.

In one particular example, nanopore device 300 of FIG. 3 is a alpha hemolysin (αHL) nanopore device having a single αHL protein embedded in a diphytanoylphosphatidylcholine (DPhPC) lipid bilayer 302 formed over a lipid bilayer compatible silver-gold alloy surface 304 coated on a copper material 306. The lipid bilayer compatible silver-gold alloy surface 304 is isolated by lipid bilayer incompatible silicon nitride surfaces 305, and the copper material 306 is electrically insulated by silicon nitride materials 307. The copper 306 is coupled to electrical circuitry 322 that is integrated in a silicon substrate 328. A silver-silver chloride electrode placed on-chip or extending down from a cover plate contacts an aqueous solution containing dsDNA molecules.

The αHL nanopore is an assembly of seven individual peptides. The entrance or vestible of the αHL nanopore is approximately 26 Å in diameter, which is wide enough to accommodate a portion of a dsDNA molecule. From the vestible, the αHL nanopore first widens and then narrows to a barrel having a diameter of approximately 15 Å, which is wide enough to allow a single ssDNA molecule to pass through but not wide enough to allow a dsDNA molecule to pass through. At a given time, approximately 1-20 DNA bases can occupy the barrel of the αHL nanopore.

In addition to DPhPC, the lipid bilayer of the nanopore device can be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methylester (DOPME), diphytanoylphosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the αHL nanopore shown above, the nanopore may be one of various other types of nanopores; examples include γ-hemolysin, leukocidin, melittin, and various other naturally occurring, modified natural, and synthetic nanopores. A suitable nanopore may be selected based on various characteristics of the analyte molecule, such as the size of the analyte molecule in relation to the pore size of the nanopore. For example, the αHL nanopore is a nanopore that has a restrictive pore size of approximately 15 Å. It is suitable for analyzing DNA molecules since it allows a single strand DNA (ssDNA) to pass through while restricting a double strand DNA (dsDNA).

Figure 4A:
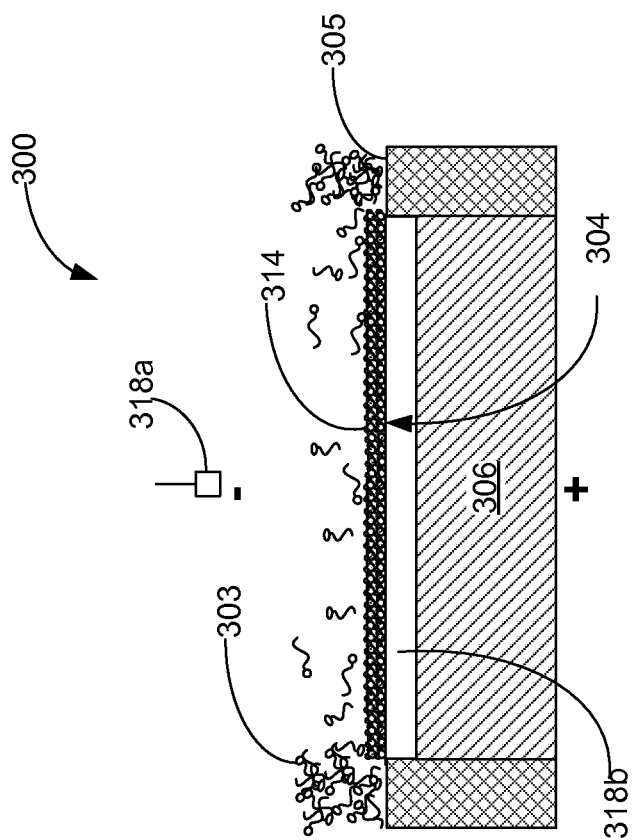
FIG. 4A is a diagram illustrating that nanopore device 300 is in a state in which a lipid bilayer has not yet been formed.
Figure 4B:
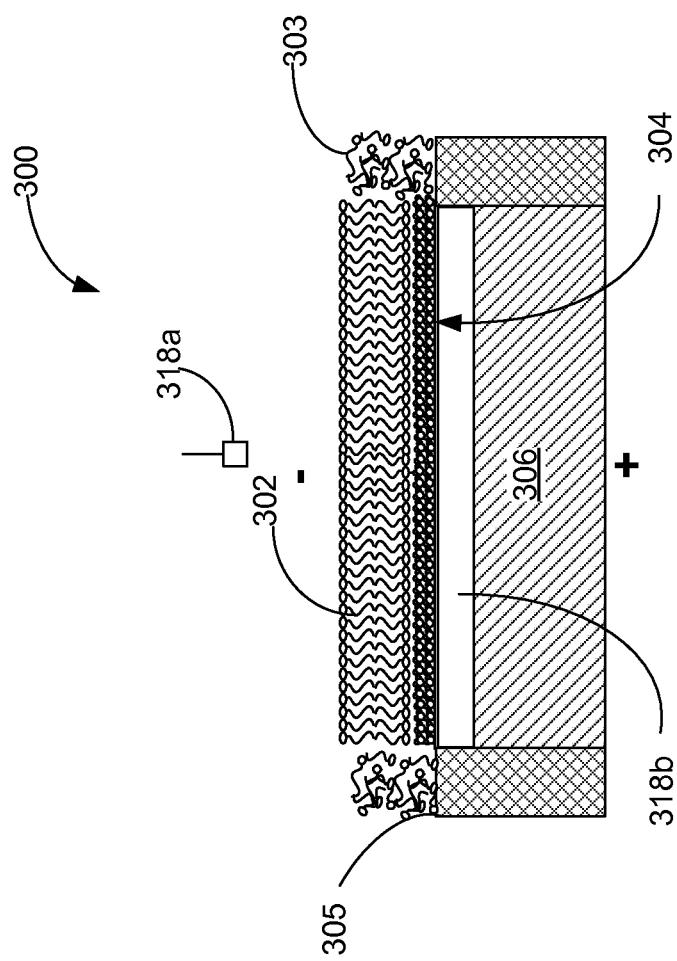
FIG. 4B is a diagram illustrating that nanopore device 300 is in a state in which a lipid bilayer 302 has been formed.
Figure 4C:
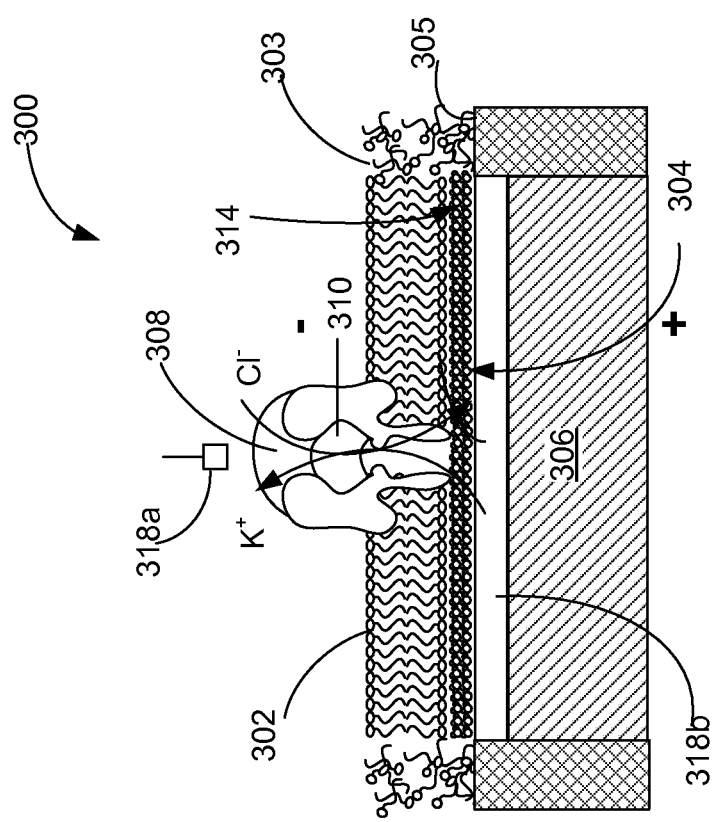
FIG. 4C is a diagram illustrating that nanopore device 300 is in a state in which a nanopore structure 308 with a nanopore 310 has been inserted into lipid bilayer 302.

FIGS. 4A-4C illustrate three different states of nanopore device 300. FIG. 4A is a diagram illustrating that nanopore device 300 is in a state in which a lipid bilayer has not yet been formed. FIG. 4B is a diagram illustrating that nanopore device 300 is in a state in which a lipid bilayer 302 has been formed. FIG. 4C is a diagram illustrating that nanopore device 300 is in a state in which a nanopore structure 308 with a nanopore 310 has been inserted into lipid bilayer 302.

Figure 5:
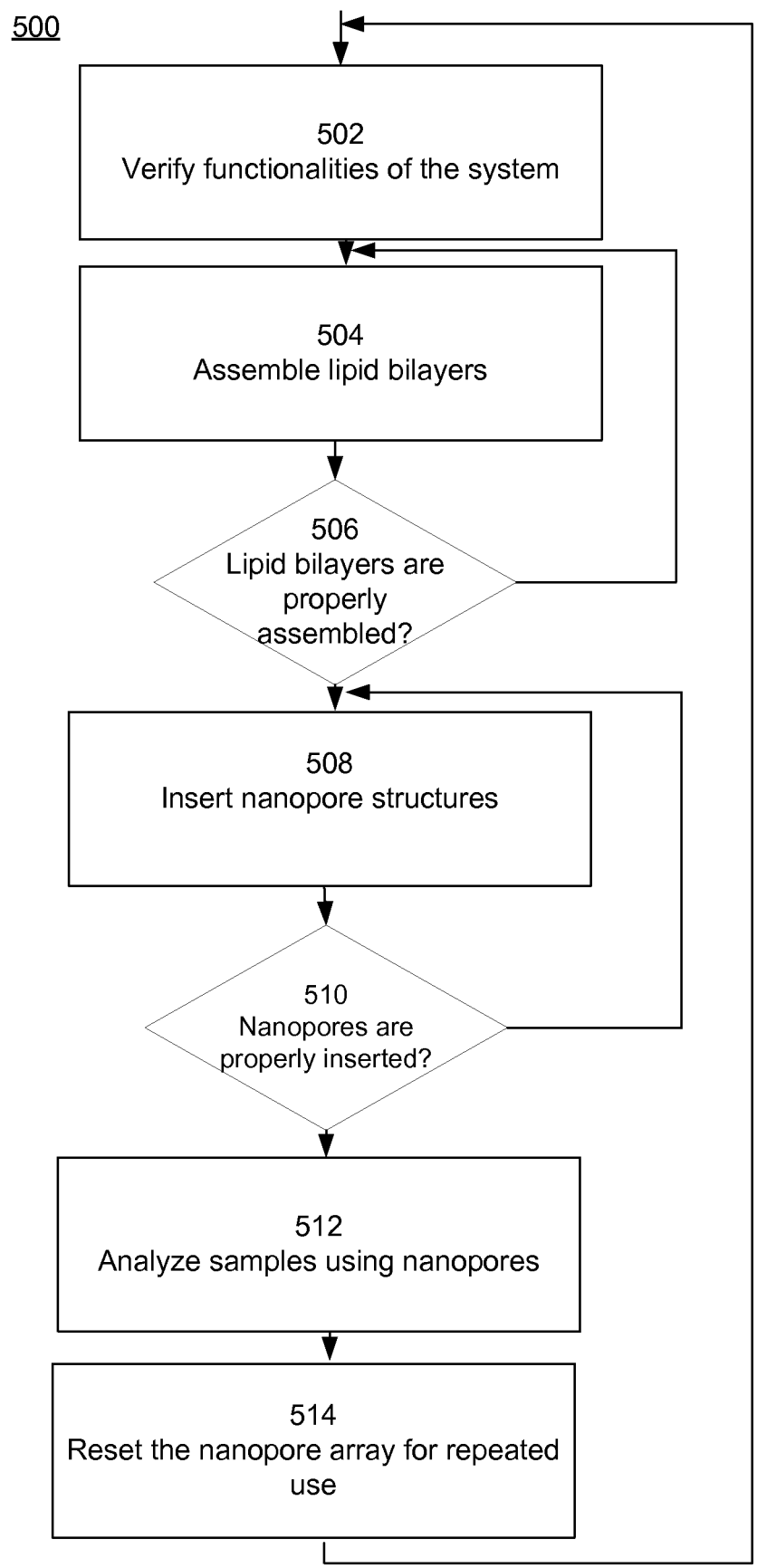
FIG. 5 is a flow diagram illustrating an embodiment of a process 500 for analyzing molecules using nanopore devices.

FIG. 5 is a flow diagram illustrating an embodiment of a process 500 for analyzing molecules using nanopore devices. In some embodiments, process 500 is a process that is performed by system 100 of FIG. 1.

At 502, various functionalities of system 100 are verified. In some embodiments, master controller 104 may send test signals to the modules of system 100, including nanopore array 102, temperature controller 106, and fluidic system 108. In response, each module may perform verification steps at the module. For example, nanopore array 102 may measure the current flowing in a particular nanopore device. After the verification steps are performed at the modules, each of the modules may send a response back to master controller 104 for verification purposes. Depending on the responses received from the various modules, master controller 104 may determine whether further verifications are needed. In some embodiments, the verification results may be stored in a log file. In some embodiments, if master controller 104 has detected any errors, then an alarm may be triggered or process 500 may be terminated.

In some embodiments, verification of the different modules may be performed at different levels, and the levels may be configurable. For example, master controller 104 may verify the functionalities of nanopore array 102 at the printed circuit board level or at the semiconductor chip level. In some embodiments, master controller 104 may verify the functionalities of a group of cells. If the number of cells within the group that are functioning properly falls below a certain threshold, then master controller 104 may determine that the group of cells is mal-functioning and that the group of cells should be disabled.

At 504, lipid bilayers are assembled. In some embodiments, master controller 104 may cause fluidic system 108 to deliver a lipid forming reagent to the cells of nanopore array 102. The lipid forming reagent is then deposited on lipid bilayer compatible surface 304 within a cell. As discussed above, the lipid bilayer may be formed using different materials, including different amphiphilic materials. Depending on the type of lipid bilayers to be formed, master controller 104 may cause different stimuli (e.g., electrical, temperature, chemical, or gas) to be applied to the cells to facilitate the assembling of the lipid bilayers.

At 506, it is determined whether the lipid bilayers are properly formed. Depending on the type of lipid bilayers to be formed, different physical or electrical property measurements (e.g., resistance, current, or capacitance measurements) may be made at the cells and then sent to master controller 104 via signal lines 114 for determining whether lipid bilayers are properly assembled. In some embodiments, steps 504 and 506 are repeated until master controller 104 has determined that lipid bilayers have been properly assembled in a minimum number of cells in nanopore array 102. In some embodiments, if the number of cells with lipid bilayers properly assembled falls below a certain threshold after a fixed period of time, master controller 104 may terminate process 500. In addition, an alarm may be triggered or an error message may be written to the log file. In some embodiments, if the number of cells with lipid bilayers properly assembled is above a certain threshold, master controller 104 may cause system 100 to proceed to step 508.

At 508, nanopore structures with nanopores are inserted. In some embodiments, master controller 104 may cause fluidic system 108 to deliver a nanopore forming reagent (e.g., a solution containing α-hemolysin) to the cells of nanopore array 102. Master controller 104 may cause different stimuli (e.g., electrical, temperature, chemical, or gas) to be applied to the cells to facilitate the insertion of the nanopore structures into the lipid bilayers.

At 510, it is determined whether the nanopore structures are properly formed. Depending on the type of nanopores to be formed, different measurements (e.g., resistance, current, or capacitance measurements) may be made at the cells and then sent to master controller 104 via signal lines 114 for determining whether nanopores are properly inserted. In some embodiments, steps 508 and 510 are repeated until master controller 104 has determined that nanopores have been properly inserted in a minimum number of cells in nanopore array 102. In some embodiments, if the number of cells with nanopores properly inserted falls below a certain threshold after a fixed period of time, master controller 104 may terminate process 500. In addition, an alarm may be triggered or an error message may be written to the log file. In some embodiments, if the number of cells with nanopores properly inserted is above a certain threshold, master controller 104 may cause system 100 to proceed to step 512.

At 512, samples are analyzed using the nanopores in nanopore array 102. In some embodiments, master controller 104 may cause fluidic system 108 to deliver samples to the sample chambers 316 in nanopore array 102. Depending on different factors, including the type of samples that are being analyzed and the type of nanopores formed, master controller 104 may cause different stimuli (e.g., electrical, temperature, chemical, or gas) to be applied to the cells to facilitate the manipulating, detecting, correlating, characterizing, analyzing and/or sequencing of molecules in the nanopores. Different measurements (e.g., resistance, current, or capacitance measurements) may be made at the cells and then sent to master controller 104 via signal lines 114. Master controller 104 may use the received measurements to detect, correlate, determine, characterize, sequence and/or discriminate various structural and chemical features of a molecule as the molecule stays inside the nanopore, traverses through the nanopore, or interacts with the nanopore.

At 514, nanopore array is reset and re-initialized for repeated uses. In some embodiments, nanopore array 102 may be reused multiple times. For example, nanopore array 102 may be used for analyzing different types of samples during different runs. In another example, nanopore array 102 may be reused for analyzing a single type of samples over multiple runs. New nanopores may be reformed in nanopore array 102 such that nanopore array 102 may be reused. New nanopores may be reformed in nanopore array 102 after the contents (e.g., lipid bilayers with nanopores inserted, lipid bilayers without nanopores inserted, and samples) in nanopore array 102 have been flushed out or rinsed out (e.g., using saline solution) by master controller 104 and fluidic system 108.

In some embodiments, master controller 104 may detect and determine whether there are any molecules or other contents of interest remaining in the cells of nanopore array 102. Master controller 104 and fluidic system 108 may selectively rinse out the contents (e.g., lipid bilayers) within cells in which no molecules or other contents of interest are found. The molecules or other contents of interest in the remaining cells may be retrieved. In one example, the molecules may be retrieved manually. In another example, master controller 104 and fluidic system 108 may deliver the molecules or other contents of interest to storage device 110 before the remaining contents are rinsed out. After 514, nanopore array 102 is ready for repeated uses again, and process 500 may be restarted at 502. In some embodiments, step 514 is performed before a nanopore array 102 is used for the first time. For example, nanopore array 102 is rinsed with saline solution before the functionalities of system 100 is checked at 502.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for analyzing a plurality of molecules, the system comprising:
   a nanopore array including a plurality of cells included on a chip;
   a fluidic system configured to send one or more reagents to the nanopore array;
   a data interface configured to receive measurements from the plurality of cells; and
   a master controller, the master controller programmed to:
   assemble lipid bilayers in the plurality of cells;
   insert nanopores into the assembled lipid bilayers;
   determine states of the plurality of cells based on measurements from the plurality of cells;
   analyze a sample using the inserted nanopores; after analyzing the sample; direct the fluidic system to rinse out the contents within the cells;
   assemble new lipid bilayers in the plurality of cells;
   insert nanopores into the new lipid bilayers;
   determine states of the plurality of cells with the new lipid bilayers based on measurements from the plurality of cells; and
   analyze a second sample using the nanopores inserted into the new lipid bilayers.

2. The system of claim 1, further comprising a memory that stores information about the states of the plurality of cells.

3. The system of claim 1, wherein the master controller is further configured to determine when to receive measurements from the nanopore array.

4. The system of claim 3, wherein at least a portion of the measurements from the nanopore array is used to analyze the molecules.

5. The system of claim 1, wherein a state for each cell includes one of the following: a lipid bilayer is not formed, a lipid bilayer is formed, and a nanopore is formed.

6. The system of claim 1, wherein the one or more reagents include the plurality of molecules.

* * * * *